United States Patent [19]
Christner et al.

[11] Patent Number: 5,939,329
[45] Date of Patent: Aug. 17, 1999

[54] TEST STRIP INCUBATION DEVICE AND METHOD

[75] Inventors: James E. Christner, Elkhart; Kenneth W. Price, Granger, both of Ind.

[73] Assignee: Serim Research Corporation, Elkhart, Ind.

[21] Appl. No.: 09/074,532

[22] Filed: May 7, 1998

Related U.S. Application Data

[60] Provisional application No. 60/046,500, May 14, 1997.

[51] Int. Cl.$^6$ .................................................. G01N 21/03
[52] U.S. Cl. ...................... 436/165; 436/164; 436/168; 422/58; 422/61
[58] Field of Search ........................ 422/58, 61; 436/44, 436/47, 63, 164, 165, 168–169

[56] References Cited

U.S. PATENT DOCUMENTS

| | | | |
|---|---|---|---|
| 4,820,491 | 4/1989 | Khoja et al. | 436/46 |
| 5,122,343 | 6/1992 | Ishizaka et al. | 436/44 |
| 5,178,835 | 1/1993 | Uekusa et al. | 436/44 |
| 5,686,047 | 11/1997 | Augstein | 436/44 |

Primary Examiner—Lyle A. Alexander
Attorney, Agent, or Firm—Baker & Daniels

[57] ABSTRACT

A test strip incubation device and method for developing a test strip having a reagent test pad disposed thereon, the reagent test pad requiring an incubation time, which allows greater accuracy and reliability of test results as well as a narrower window of PASS and FAIL indication concentrations. The device comprises a test strip holder which allows a wetted reagent test pad to be vertically stored in an enclosed reaction chamber during the incubation period. The reaction chamber is bounded by a substantially clear material to allow the user to easily observe the status of the reagent test pad held in the reaction chamber. The enclosed reaction chamber provides a high humidity environment for minimizing water evaporation from the reagent test pad during the incubation period. The device may be economically formed from low cost materials, is simple to use and facilitates disposal of the sample material after testing. The device is advantageously used in combination with a storage device which includes recesses for easy storage of several devices and allows viewing of the reagent test pads. The method comprises the steps of wetting the reagent test pad and vertically placing the reagent test pad in an enclosed reaction chamber during the incubation period. The enclosed reaction chamber provides a high humidity environment for minimizing the evaporation of water from the reagent test pad.

7 Claims, 3 Drawing Sheets

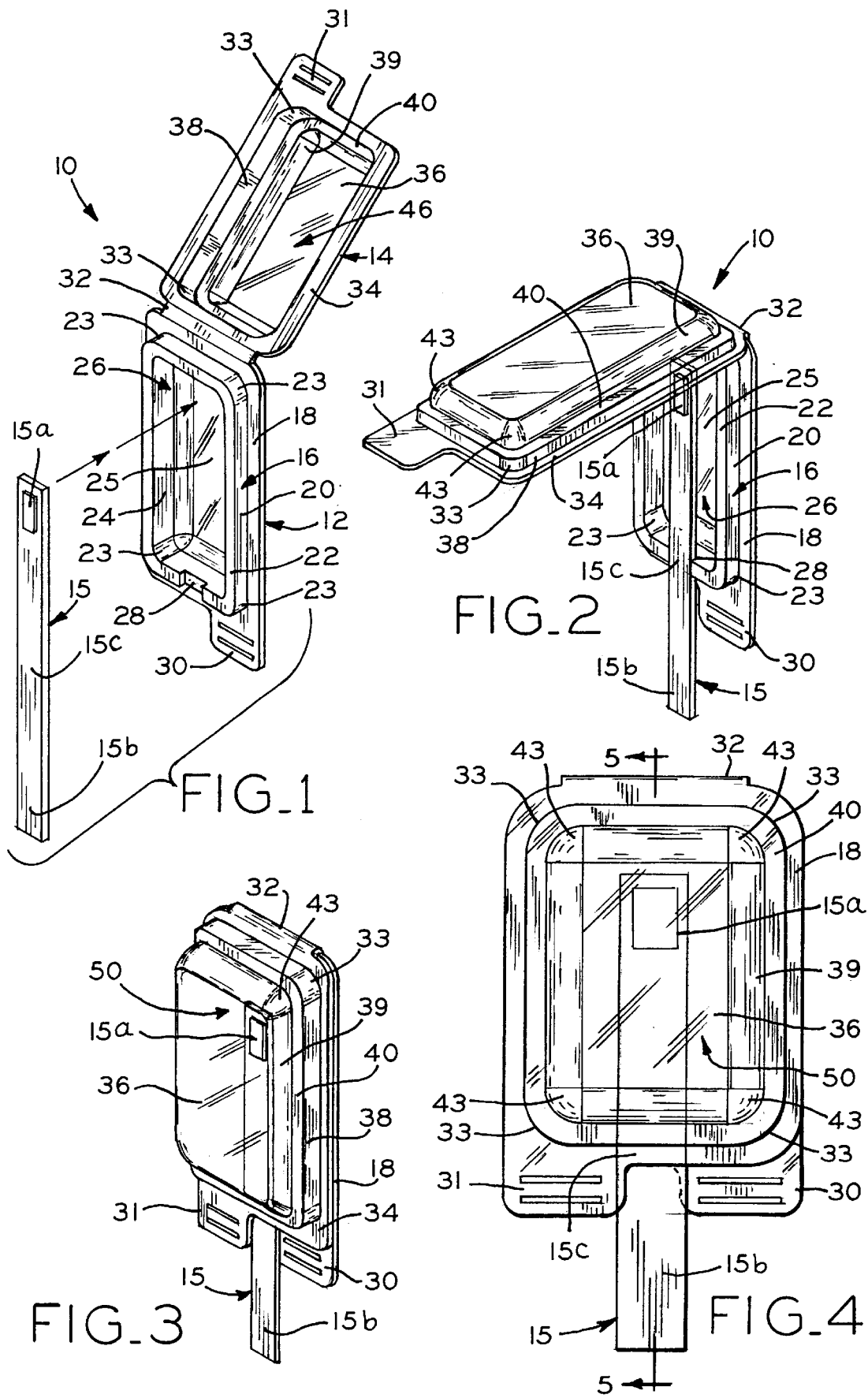

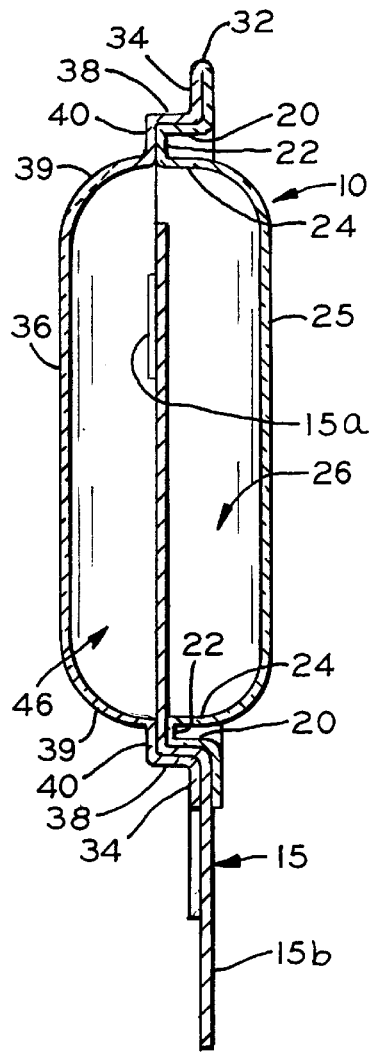
FIG_5
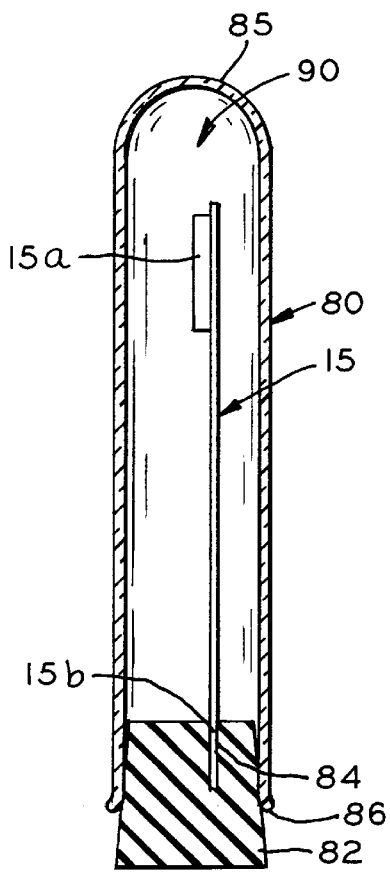
FIG_7
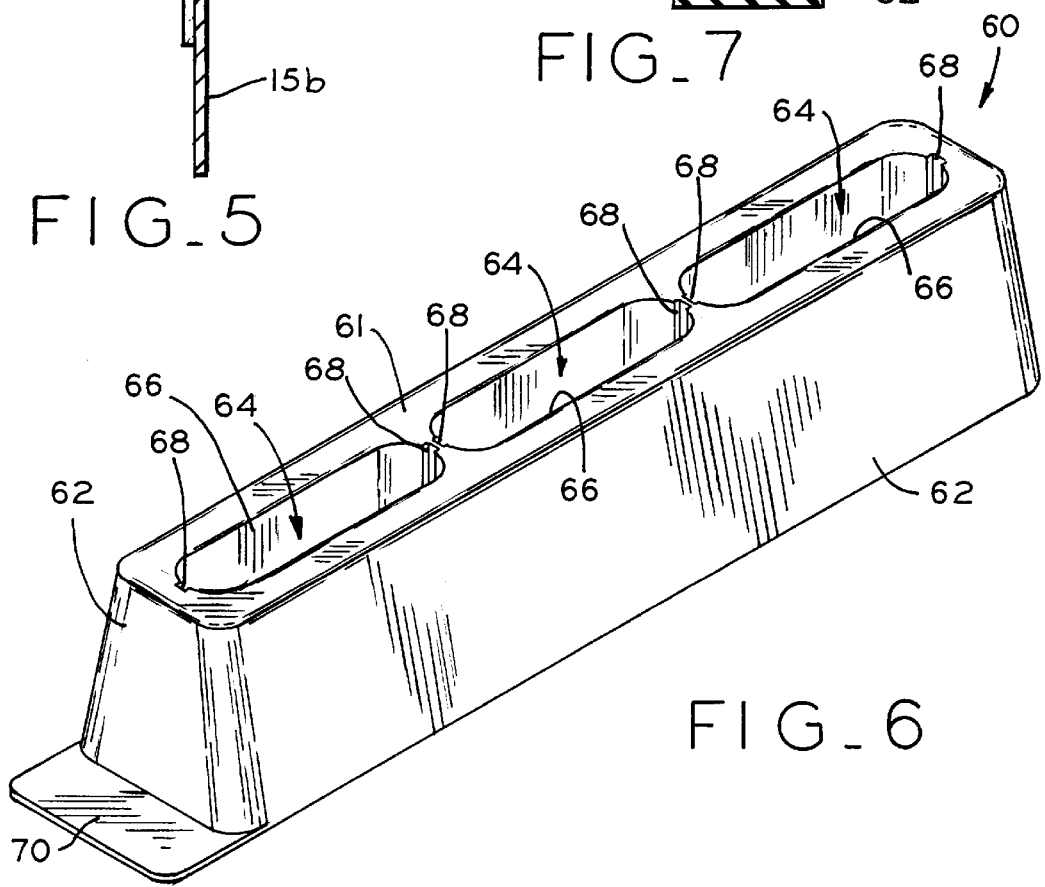
FIG_6

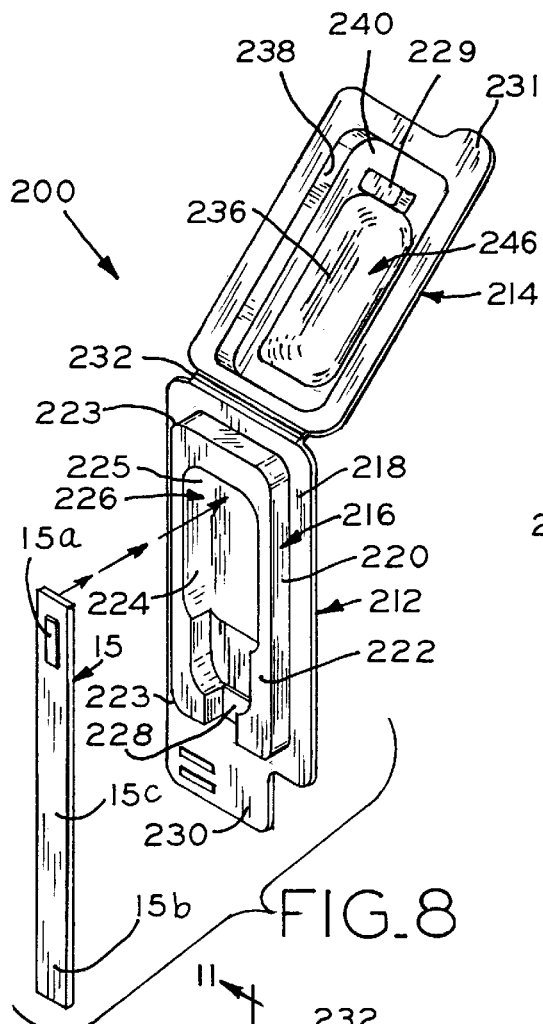
FIG_8
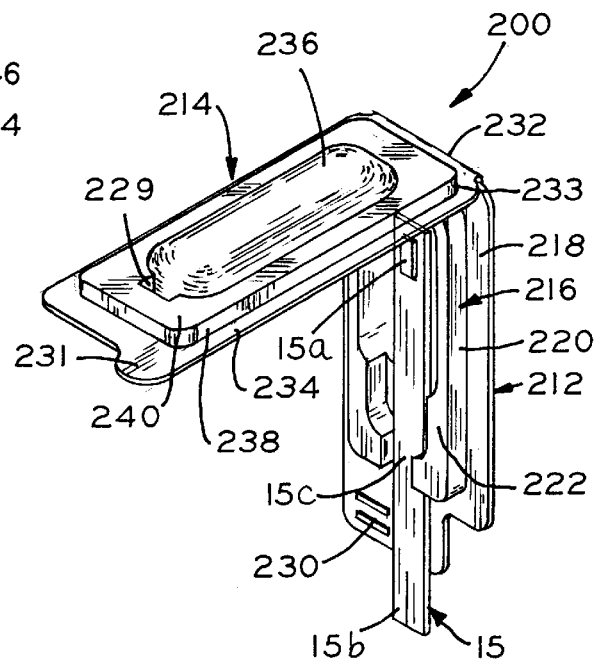
FIG_9
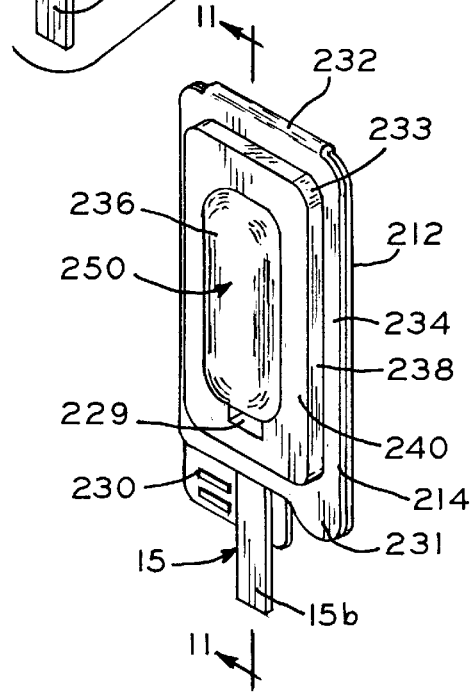
FIG_10
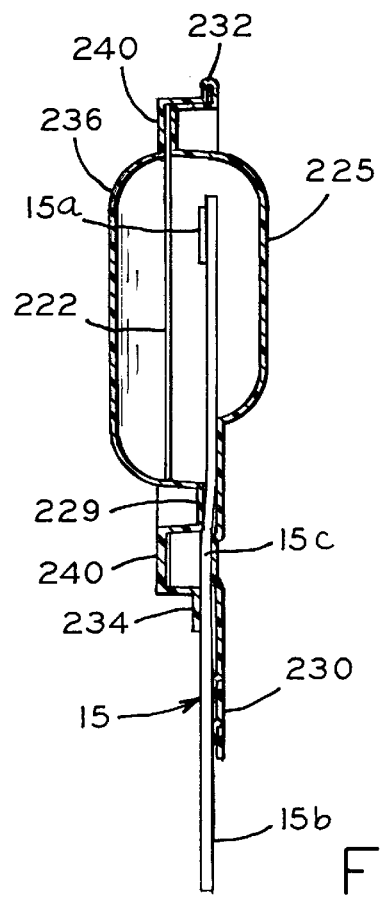
FIG_11

TEST STRIP INCUBATION DEVICE AND METHOD

This application claims benefit of Provisional Appln 60/046,500 filed May 14, 1997.

BACKGROUND OF THE INVENTION

1. Field of the Invention

The present invention relates to a method and an apparatus for developing a test strip, and more particularly a test strip having a reagent test pad requiring an incubation period for developing the desired test results disposed thereon.

2. Description of the Related Art

Test strips having a reagent test pad disposed thereon are conventionally known testing devices which are often used to determine whether a sufficient concentration of a chemical or chemicals is present in a solution. In the conventionally known procedure, the reagent test pad having reagent chemicals disposed thereon is placed in contact with a solution to be tested, typically by dipping the test strip in the solution. When the reagent test pad is sufficiently wetted, the test pad is removed from the solution and the indication on the test pad is examined after a predetermined waiting time. The reagent test pad is usually designed to change to a particular color or range of colors corresponding to the concentration of the chemicals in the solution being examined. In conventionally known procedures, the user places the wetted test pad in an open environment, such as on a lab bench, while waiting for the color change to develop.

Although simple to use, one consideration in using such test strips is the accuracy and reliability of the color indications developed on the reagent test pads. In conventional applications, a standardized chart showing various colors and corresponding concentrations is provided. To be effective and reliable, the test performed should always produce a color which corresponds to an accurate concentration of the chemical being tested. In other words, the person performing the test should be able to confidently match the color produced by the test strip with a corresponding color on the standardized chart and the concentration of chemical then taken therefrom.

Unfortunately, due to the imprecision inherent in any analytical tests, the desired indication may be observed at concentrations other than the predetermined concentration. For example, in a test producing a mere change in color at a given concentration, such color change could incorrectly occur at a concentration other than the given concentration. The concentration at which the test always reads "PASS" or "FAIL" is determined by the properties and conditions of the test. The difference in the 100% FAIL and the 100% PASS concentration may be called the "window". It is desirable to have the range of this window be as small as possible to ensure effective management and use of the solutions being tested, for example to ensure that only effective solutions are used and to ensure that effective solutions are not needlessly replaced.

The window may be narrowed in many tests by increasing the reaction time between the chemicals in the reagent test pad and the chemicals in the solution. This is most likely due to two factors associated with dry reagents tests, namely 1) the reactants on the test strip need time to completely dissolve, and 2) the diffusion of reactants in a solid matrix is very slow. However, because these reactions occur in aqueous solutions, the reaction time available for the test is limited by the evaporation of water from the reagent test pad. Accurate measurement within a narrow window is difficult if the moisture necessary to maintain the reagents in solution evaporates from the reagent test pad before the reaction is complete. This is particularly true when measuring highly concentrated analytes where the loss of even small amounts of water may cause precipitation of analytes and/or reactants within the test pad.

Conventionally known methods and apparatuses are limited in their ability to obtain accurate and reliable results within a narrow window because the water necessary to maintain the reagents in solution typically evaporates from the test pad before allowing a sufficient incubation period. This evaporation leads to improper use of ineffective solutions as well as wasteful replacement of effective solutions.

Therefore, what is needed is an accurate and reliable method and apparatus for using test strips described above wherein a sufficient incubation period is provided to allow the reagents to completely react with one another before the requisite moisture evaporates from the test pad.

SUMMARY OF THE INVENTION

The present invention is a method and an apparatus for providing accurate and reliable results from a test strip having a reagent test pad disposed thereon when the reagent test pad requires an incubation period for the reagents to react. The present invention also provides a more narrow window between PASS and FAIL indications which in turn allows effective use and management of the test solutions. The present invention achieves these results by placing and maintaining the reagent test pad in an enclosed, high humidity environment, in a substantially vertical orientation during the incubation period.

The method of the present invention comprises, in one form thereof, the steps of providing a test strip having a reagent test pad disposed on one end and a grip portion disposed on another end. The reagent test pad is wetted with a desired test material and placed in an enclosed chamber and after a predetermined waiting period, the results indicated on the reagent test pad are read. The enclosed chamber is advantageously adapted to provide a high humidity environment and the reagent test pad is advantageously maintained in a vertical manner in the enclosed chamber during the incubation period.

In another form, the present invention comprises a test strip holder of reagent test strips having a reagent test pad requiring an incubation period comprising a base and a cover, the base and cover adapted to fittingly engage each other to form an enclosed reaction chamber. The enclosed reaction chamber is adapted to store the reagent test pad. One of the base and cover includes a holding portion adapted to engage the test strip to thereby securely maintain the reagent test pad in the reaction chamber. One of the first and second holders includes a substantially clear portion allowing viewing of the test strip.

The present invention also comprises, in another form thereof, a combination comprising a test strip having a reagent test pad disposed thereon, the reagent test pad requiring an incubation period, and a test strip holder, the test strip holder comprising a base and a cover. The base and cover are adapted to fittingly engage each other to form an enclosed reaction chamber. The enclosed reaction chamber is adapted to receive and hold the reagent test pad and one of the base and cover includes a substantially clear portion allowing viewing of the reagent test pad.

Additionally, a test strip storage device may advantageously be provided for use with the test strip holder of the present invention wherein the test strip storage device includes a storage element disposed on a pedestal, the storage element having a plurality of recesses formed on a top surface thereof for placement of the test strip holders therein in a manner which allows the user to easily store the test strip holder and view the indication on the reagent test pad.

Therefore, it is an objective of the present invention to provide a method and an apparatus for accurately checking the concentration of a chemical in a solution using a test strip reagent pad.

It is also an objective of the present invention to provide a method and an apparatus for accurately checking the concentration of a chemical in a solution using a test strip pad having a reagent test pad which requires an incubation period.

It is also an objective of the present invention to provide a method and an apparatus which permits a reagent test pad to be vertically stored in a high humidity environment for a sufficient period of time to allow the reactants to fully react.

It is also an objective of the present invention to provide a method and an apparatus which allows a very narrow window between the 100% FAIL and the 100% PASS indications on the reagent test pad.

It is also an objective of the present invention to provide a method and an apparatus which accomplishes the above cited objectives in a simple, easy to use, economical manner.

It is also an objective of the present invention to provide a disposable or reusable apparatus which accomplishes the above cited objectives.

BRIEF DESCRIPTION OF THE DRAWINGS

The above mentioned and other features and objects of this invention, and the manner of attaining them, will become more apparent and the invention itself will be better understood by reference to the following description of the embodiment of the invention taken in conjunction with the accompanying drawings, wherein:

FIG. 1 is a perspective view of an embodiment of a test strip holder of the present invention in the open position and a test strip having a reagent test pad disposed thereon;

FIG. 2 is a perspective view of a test strip placed in the test strip holder of FIG. 1 of the present invention which has been moved toward the closed position;

FIG. 3 is a perspective view of a test strip placed in the test strip holder of FIG. 1 of the present invention which is in the closed position;

FIG. 4 is a front elevational view of the test strip held in the test strip holder of FIG. 1 of the present invention;

FIG. 5 is a sectional view taken along line 5—5 of FIG. 4;

FIG. 6 is a perspective view of a storage device for storing test strip holders of the present invention;

FIG. 7 is a cross-sectional view of an alternative embodiment of the test strip holder of the present invention;

FIG. 8 is a perspective view of an alternative embodiment of a test strip holder of the present invention in the open position and a test strip having a reagent test pad disposed thereon;

FIG. 9 is a perspective view of a test strip placed in the test strip holder of FIG. 8 of the present invention which has been moved toward the closed position;

FIG. 10 is a perspective view of a test strip placed in the test strip holder of FIG. 8 of the present invention which is in the closed position; and FIG. 11 is a cross sectional view along line 11—11 of FIG. 10.

Corresponding reference characters indicate corresponding parts throughout the several views. Although the drawings represent embodiments of the present invention, the drawings are not necessarily to scale and certain features may be exaggerated in order to better illustrate and explain the present invention. The exemplifications set out herein illustrate embodiments of the invention, in several forms, and such exemplifications are not to be construed as limiting the scope of the invention in any manner.

DETAILED DESCRIPTION OF THE INVENTION

The embodiments disclosed below are not intended to be exhaustive or limit the invention to the precise forms disclosed in the following detailed description. Rather, the embodiments are chosen and described so that others skilled in the art may utilize their teachings.

Referring now to FIGS. 1–5, test strip holder 10 of the present invention comprises base 12 and cover 14 which are integrally connected by flexible connection 32. Base 12 and cover 14 are configured and adapted to engage each other to form an enclosed reaction chamber for holding test strip 15. As particularly shown in FIGS. 1–2 and further described below, base 12 and cover 14 can pivot with respect to each other about the axis of flexible connection 32 in order to form sealed reaction chamber 50 which provides a high humidity environment for minimizing the evaporation of water from test strip 15 during the incubation period of the test. A typical test strip 15 suitable for use with test strip holder 10 includes reagent test pad 15a, grip portion 15b and middle portion 15c.

Base 12 comprises substantially rectangular back panel 25 having raised edge 16 disposed around the periphery thereof. Raised edge 16 is in a spaced apart relationship from the edge of back panel 25 along shoulder 18. Raised edge 16 comprises outer sidewalls 20, top wall 22, and inner sidewalls 24. Rounded corner portions 23 are disposed along the four corners of raised edge 16 and interconnect the linear portions of raised edge 16. Back panel 25 in combination with raised edge 16 define recessed space 26. As described further below, recessed space 26 is used in combination with recessed space 46 of cover 14 to form reaction chamber 50. Also, indentation 28 is disposed on a lower portion of raised edge 16. Indentation 28 is adapted to fittingly receive test strip 15 and maintain test strip 15 in a vertically held position after base 12 and cover 14 have been joined. Thus, in the present embodiment, indentation 28 comprises a holding portion for test strip 15. Although the present embodiment uses a notched arrangement as a holding portion for test strip 15, it is to be understood that any conventionally known method for securely holding test strip 15 in holder 10 may be used, for example raised portions on base 12 or cover 14 as described hereinbelow, or adhesive elements disposed on base 12 or cover 14.

Back panel 25 further includes handle 30 disposed at a lower end thereof to provide an easy handling mechanism for the user. It is to be understood that although handle 30 is only on one corner of back panel 25, other handling mechanisms may be placed in many locations around back panel 25 to facilitate the handling of back panel 25.

Cover 14 is integrally connected with base 12 via flexible connection 32 and is adapted to fittingly engage base 12. As shown in FIGS. 1–3, cover 14 comprises front panel 36 which is integrally joined with flat edge portion 34 via sidewalls 38, flat portion 40 and rounded shoulder portion 39. The combination of front panel 36, rounded shoulders 39, sidewall 38, and flat portion 40 defines recessed space 46. Straight line portions of sidewall 38 are joined by rounded comers 33 and straight line portions of rounded shoulder 39 are joined by rounded comers 43. Front panel 36 included handle 31 to provide an easy handling mechanism for the user. Front panel 36 is made of a relatively clear, see-through plastic, such that a user can easily look through front panel 36 to check the indication on reaction portion 15a of test strip 15.

The dimensions of raised edges 16, particularly rounded portions 23, and sidewalls 38, particularly comer portions 43, are sized and adapted to fittingly engage each other such that base 12 and cover 14 snap tight. It is to be understood that any conventionally known method for achieving a snap tight engagement of base 12 and cover 14 may be used, for example, the area encompassed by outer sidewall 20 may be slightly larger than the are encompassed by sidewall 38, or rounded comers 23 may bulge out slightly wider than the inside areas of rounded comers 33, or sidewall 38 and sidewall 20 may fittingly contact each other and outer movable snaps may be placed on the edges of flat portions 18 or 34 to achieve the snap tight engagement.

The snap tight engagement of base 12 and cover 14 combines recessed spaces 26 and 46 to form enclosed chamber 50. Enclosed chamber 50 is sealed sufficiently to provide a high humidity environment for minimizing water evaporation from reagent test pad 15a while holding test strip 15 for a required incubation period.

With reference to FIG. 6, test strip holder 10 is advantageously used in combination with holder device 60 which can be used for storing and maintaining a plurality of test strip holders 10 in a vertical position while waiting for an indication to develop on test strip 15. Holder device 60 is a receptacle comprising top wall 61 and sidewalls 62 disposed on pedestal 70. Recesses 64 having inner walls 66 are disposed in top wall 61 to receive and hold test strip holder 10. Recesses 64 are oriented along the length of top wall 61 and have a depth wherein clear front panel 36 of a test strip holder 10 placed therein can be easily viewed by a user. Also, notches 68 are disposed along the ends of inner walls 66 to facilitate the insertion of test strip holder 10 into recess 64. It is to be understood that although holding device 60 shown in FIG. 6 comprises three recesses 64, it is possible to have holding device 60 which includes any suitable number of recesses 64, aligned as desired to provide easy viewing of front panel 36 by the user.

The method for using test strip 15 with test strip holder 10 to test for the concentration of in a test solution is now described. The user initially holds grip portion 15b and dips reagent test pad 15a into the test solution and then withdraws reagent test pad 15a from the test solution after reagent test pad 15a has been sufficiently wetted. Test strip 15 is then transferred to test strip holder 10 and held against test strip holder 10 by placing intermediate portion 15c against indentation 28 of base 12. While continuing to hold intermediate portion 15c against indentation 28, the user rotates cover 14 about the axis of pivot connection 32 until the associated surfaces of base 12 and cover 14 come in contact with each other. The user then snaps together base 12 and cover 14 to form enclosed reaction chamber 50 and to thereby secure test strip 15, particularly reagent test pad 15a, therein. At this point, reaction portion 15a is vertically disposed inside enclosed chamber 50 which maintains a high humidity environment for minimizing the evaporation of water from reagent test pad 15a.

The vertical alignment of test strip 15 allows excess solution on reagent test strip pad 15 to fall off test pad 15 by gravity to provide more consistent test results. Previously, excess solution on a reagent test pad formed a bead which was removed by either shaking off the excess or blotting the test pad with an absorbent material. In either method, the amount of solution which was removed from the test pad varied greatly such that the test results also varied greatly. Storing test strip holder 10 in a vertical position obviates this problem as the excess solution falls off test pad 15 by gravity flow and a consistent amount of solution remains on test pad 15, thereby resulting in more consistent results.

Once test strip 15 has been secured onto test strip holder 10 as described above, the user may continue to hold test strip holder 10 in a vertical position until the incubation period has elapsed or may place and store test strip holder 10 in holder device 60. To place test strip holder 10 in holder device 10, the sides of test strip holder 10 are aligned with notches 68 of recess 64 and test strip holder 10 is slidingly placed into recess 64. Holder device 60 or equivalent may be aligned to face the user to facilitate the reading of the indication on reagent test pad 15a. In this manner, test strip holder 10 is maintained in a vertical position and front panel 36 faces outward such that the user can readily observe any color changes on reagent test pad 15a.

Once the test is completed, the entire assembly may be discarded without the user coming in contact with the test solution or the reagent test pad. In this manner, the present method and apparatus facilitates the disposal of the test products.

An alternative embodiment of the present invention is shown in FIG. 7 wherein clear tube 80, for example a test tube, serves as a cover and stopper 82 provides a base. In combination, tube 80 and stopper 82 provide a sealed, high humidity chamber for developing a reagent test pad. In the embodiment shown in FIG. 7, slot 84 is disposed on stopper 82 for holding test strip 15 in a vertical manner during the incubation period. Here, end portion 15b of test strip 15 is inserted into slot 84 and then stopper 82 is partially inserted into open end 86 of test tube 80 to form enclosed reaction chamber 90 for holding reagent test pad 15a therein. Once test strip 15 has been placed in tube 80, tube 80 may be left in the vertical position until the incubation period has elapsed. The user can then easily view any indication changes on reagent test pad 15a through tube 80.

An alternative embodiment of the present invention is shown in FIGS. 8–11 wherein test strip holder 200 comprises base 212 and cover 214 which are integrally connected by flexible connection 232. Base 212 and cover 214 are configured to engage each other to form an enclosed reaction chamber for holding test strip 15. As particularly shown in FIGS. 8–9 and further described below, base 212 and cover 214 can pivot with respect to each other about the axis of flexible connection 232 in order to form sealed reaction chamber 250 which provides a high humidity environment for minimizing the evaporation of water from test strip 15 during the incubation period of the test. Base 212 comprises bottle-shaped back panel 225 having raised edge 216 disposed around the periphery thereof. Raised edge 216 is spaced apart from the edge of back panel 225 along shoulder 218. Raised edge 216 comprises outer side walls 220, top wall 222 and inner side walls 224. Rounded comer portions 223 are disposed along the four outside comers of raised edge 216. Back panel 225 in combination with raised edge 216 define recessed space 226. Recessed space 226 combined with recess space 246 in cover 214 form reaction chamber 250.

Indentation 228 is disposed on the lower portion of raised edge 216 as shown in FIG. 8. As shown in FIGS. 9–11, indentation 228 is adapted to fittingly receive test strip 15 in a vertically held position. With reference to FIGS. 8 and 11, tab portion 229 extends from flat portion 240 of cover 214 so that when the test strip holder is closed, as shown in FIGS. 10 and 11, tab 229 serves as a holding portion to hold test strip 15 securely in place in apparatus 200. That is, tab 229 abuts against test strip 15 when cover 214 and base 212 are sealingly engaged as shown in FIG. 11.

Back panel 225 further includes handle 230 disposed at a lower end thereof to provide an easy handling mechanism for the user. Similarly, cover 214 includes handle portion 231 at a lower end thereof to provide an easier handling mechanism for the user.

Cover 214 is integrally connected with base 212 via flexible connection 232 and is adapted to fittingly engage base 212. As shown in FIGS. 8–10, cover 214 comprises front panel 236 which is integrally joined with flat edge portion 234 via sidewalls 238 and flat portion 240. A combination of front panel 236, sidewall 238 and flat portion 240 defines recess space 246. Front panel 236 is made of a relatively clear, see-through plastic, such that a user can easily look through front panel 236 to check the indication on reaction portion 15a of test strip 15. The dimensions of raised edges 216, particularly rounded portions 223, and sidewalls 238 and corner portions 233 on cover 214 are sized and adapted to fittingly engage each other such that base 212 and cover 214 snap tightly together. The snap-tight engagement of base 212 and cover 214 combines recessed spaces 226 and 246 to form enclosed chamber 250 as shown in FIG. 10.

It can be seen in the above-described embodiments that a reaction chamber for holding a reagent test pad may be provided in a simple, easy to use, disposable and economical package. It is also obvious that the apparatus may be easily manufactured using a number of inexpensive materials, including, but not limited to plastic, and a number of conventionally known processes.

The use of an enclosed reaction chamber in tests using test strips having an incubation period is effective in producing accurate test results. One test where such a method and apparatus was shown to be particularly effective is the test for determining the active concentration in chemical germicides. A typical use for chemical germicides is to disinfect or sterilize endoscopes which contain heat-sensitive optical systems. Many of the chemical germicides are reusable and used for sequential loads of instruments until the active ingredient becomes too dilute to be effective against microorganisms. Depletion of the germicide can result from dilution or chemical inactivation. The lowest concentration at which the active ingredient in the germicide will kill all test microorganisms is termed the Minimum Effective Concentration ("MEC"). The germicide is routinely tested to avoid using solutions containing less than the MEC because such solutions are ineffective.

To ensure that an ineffective solution is never used, the test should always show FAIL at the MEC. However, due to the imprecision inherent in any analytical test, FAIL results may be observed at concentrations greater than the MEC. The concentration at which the test always reads PASS is determined by the properties of the test. The difference in the 100% FAIL and the 100% PASS concentrations is the "window". It is desirable to have the window size be as small as possible to ensure that the germicide is effective and that effective germicide is not needlessly replaced. If the test frequently indicates FAIL when the disinfectant level is above the MEC, the germicide will be replaced more often than necessary.

A dry reagent test strip may be used to measure the level of the active ingredient, hydrogen peroxide, in a reusable germicide solution, for example, SPOROX®, manufactured by Reckitt & Coleman, Inc. of Montvale, N.J. The test strip comprises a reagent-containing test pad (the "indicator pad" or "pad") attached at one end of a polystyrene handle.

The chemistry of the test strip is based on the reduction of the hydrogen peroxide with a fixed amount of sulfite ion in the presence of iodide and starch. When the hydrogen peroxide concentration is 6.0% or less, it is entirely consumed by the sulfite. When its concentration is sufficient to overwhelm the reducing agent, the excess oxidizes the iodide to iodine producing a dark brown/black color in the presence of starch. The chemical reactions include the following:

$H_2O_2 + Iodide \rightarrow Iodine + H_2O$ $Iodine + Sulfite \rightarrow Iodide$ $Excess\ H_2O_2 + Iodide \rightarrow Iodine + H_2O$ $Iodine + Starch \rightarrow Starch\text{-}Iodine\ Complex\ (Brown/Black)$ It has been determined that the smaller the window, the longer the reaction period needs to be. This is most likely due to two factors associated with dry reagent tests: 1) the reactants supplied by the strip need time to completely dissolve; and 2) the diffusion of reactants in a solid matrix is very slow.

Thus, the window can be narrowed by increasing the reaction time. However, unless evaporation of water from the pad is prevented, there is an upper limit to the reaction time. A typical filter paper matrix absorbs about 0.25 ml per square inch. This means that the sample exists as a layer of about 0.5 mm thickness. The high surface area to volume ratio results in a very high relative evaporation rate. Accurate measurement is impossible if significant amounts of water evaporate from the pad prior to completion of the analytical reaction. This is particularly true when measuring highly concentrated analytes when the loss of even small amounts of water may cause the precipitation of analyte and/or reactants within the pad.

Two separate sets of tests were performed to demonstrate the effectiveness of the present invention. In the first set of tests, the test strip was developed with the reagent test pad placed in a reaction chamber. In the second set of tests, the test strips were developed with the reagent test pad left in the open.

To run the first set of tests, the test pad was dipped into the sample for a period of five seconds, removed and then placed in a vertical position with the test pad up. A reaction chamber was placed over the strip to prevent evaporation of water from the test pad. After a reaction period of 12 to 15 minutes, the color of the test pad was observed. If the solution contains 7.0% or more hydrogen peroxide, the test pad will be completely brown/black indicating a PASS result. If the solution contains 6.0% or less hydrogen peroxide, a white area will appear in the center of the test pad indicating a FAIL result. At intermediate concentrations, the strip may indicate either PASS or FAIL.

The relationship between hydrogen peroxide concentration and time to develop the FAIL result when using an enclosed reaction chamber are summarized as follows:

TABLE 1

Effect of Hydrogen Peroxide Concentration
on Time Required to Develop FAIL Result
Strips protected from evaporation

| Hydrogen Peroxide Concentration (%) | Time to Develop FAIL result (mean ± s.d., n = 10) |
|---|---|
| 5.6 | 8.3 ± 0.7 |
| 6.0 | 12.0 ± 0.8 |
| 6.6 | 18.9 ± 2.6 |
| 7.0 | all > 25 |

Based on the above, distinguishing 5.6% from 7.0% hydrogen peroxide would require a 10 minute wait, 6.0% from 7.0% a 14 minute wait and 6.6% from 7.0% a 25 minute wait. These wait times were calculated by adding 2 s.d. to the mean.

The relationship between hydrogen peroxide concentration and time to develop the FAIL result without using the enclosed reaction chamber was determined to be as follows:

TABLE 2

Effect of Evaporation
on Strip Reaction Strips not Protected from Evaporation

| Hydrogen Peroxide Concentration (%) | Time to Develop FAIL result (mean ± s.d., n = 10) |
|---|---|
| 5.6 | 18.1 ± 4.0 |
| 6.0 | all > 25 |
| 6.6 | all > 25 |
| 7.0 | all > 25 |

The results of Table 2 indicate that it would not be possible to distinguish 5.6% from 7.0% hydrogen peroxide all of the time and that it would never be possible to distinguish either 6.0% or 6.6% from 7.0%. Thus, a comparison of the two sets of test results indicates that the use of a reaction chamber to prevent water evaporation from the reagent test pad improves the strip precision considerably.

Other tests that have extended reaction times will benefit from the use of a container to prevent sample evaporation. Therefore, other test strips which may be advantageously used with the method and apparatus of the present invention include, but are not limited to, Serim DisIntek Strips for 1.0–2.5% glutaraldehyde in endoscope disinfection baths, Serim Formaldehyde Reagent Strips for 4% formaldehyde in hemodialyzer disinfectant, Serim Formaldehyde Reagent Strips for 1–2% formaldehyde in hemodialyzer disinfectant, Serim Glutaraldehyde Reagent Strips for 0.8% glutaraldehyde in hemodialyzer disinfectant, Johnson & Johnson Cidex® Solution Test Strips for 1.5–2.5% glutaraldehyde in Cidex® Activated Dialdehyde Solution, Johnson & Johnson Cidex® Plus Solution Test Strips for 1.5–3.4% glutaraldehyde in Cidex® Plus Activated Dialdehyde Solution, and Wavicide-01® Solution Test Strips for glutaraldehyde in Wavicide-01® disinfecting and Sterilizing Solution.

While this invention has been described as having an exemplary design, the present invention may be further modified within the spirit and scope of this disclosure. This application is therefore intended to cover any variations, uses, or adaptations of the invention using its general principles. For example, a clear straw or other similar tubular devices which may be held in vertical position and which reduce the evaporation of water from reagent test pad 15a may be used to provide a reaction chamber. Also, although the test strip holder of the present invention uses generally rectangular bases, it is to be understood that any shapes may be used, as long as the segments allow a snap tight engagement to form an enclosed reaction chamber for vertically holding a test strip therein. Further, this application is intended to cover such departures from the present disclosure as come within known or customary practice in the art to which this invention pertains.

What is claimed is:

1. In combination, a test strip having a reagent test pad disposed thereon, said reagent test pad requiring an incubation period, and a test strip holder, said holder formed from a single material, said test holder comprising a base and a cover, said base and said cover adapter to fittingly engage each other to form an enclosed reaction chamber capable of maintaining humidity at a desired level, said base and said cover integrally and hingedly connected to one another, said enclosed reaction chamber adapted to receive and hold said reagent test pad, one of said base and said cover including a substantially clear portion allowing viewing of said reagent test pad.

2. The combination of claim 1, wherein one of said base and said cover comprises an indentation adapted to hold said test strip.

3. The combination of claim 1, wherein one of said base and said cover comprises a tab which abuts against said test strip and securely holds said test strip.

4. The combination of claim 1, wherein said enclosed reaction chamber is adapted to hold said reagent test pad in a substantially vertical orientation.

5. The combination of claim 1, wherein at least one of said base and said cover includes a handle connected thereto and projecting therefrom, whereby said handle facilitates the engagement of said base and said cover.

6. Method for developing results on a reagent test pad disposed on a test strip and requiring an incubation period, comprising the steps of:

provicing a test strip having a reagent test pad disposed on one end and a grip portion disposed on another end;

providing a reaction chamber formed of a single material and having a base and a cover integrally and hingedly connected to one another;

wetting the reagent test pad with a desired test material;

placing the reagent test pad in the chamber and closing the chamber, whereby the humidity within the chamber is maintained at a desired level; and reading the results indicated on the reagent test pad after a predetermined waiting period.

7. The method for developing results on a reagent test pad according to claim 6, wherein said placing step comprises placing and maintaining the reagent test pad in a substantially vertical orientation in the enclosed chamber.

* * * * *

UNITED STATES PATENT AND TRADEMARK OFFICE
CERTIFICATE OF CORRECTION

PATENT NO. : 5,939,329
DATED : August 17, 1999
INVENTOR(S) : James F. Christner et al It is certified that error appears in the above-identified patent and that said Letters Patent is hereby corrected as shown below:

Claim 1, Column 10, Line 19, Delete "adapter" and substitute --adapted--therefore.

Signed and Sealed this

Fourth Day of January, 2000

Attest:

Attesting Officer      *Acting Commissioner of Patents and Trademarks*